United States Patent
Xiang et al.

(10) Patent No.: US 6,172,227 B1
(45) Date of Patent: *Jan. 9, 2001

(54) 4,5-DIAMINOPYRIMIDINE DERIVATIVES AND A METHOD FOR THE PREPARATION THEREOF

(75) Inventors: Myung Xik Xiang, Yongin; Byoung Chool Suh; Chung Keun Rhee, both of Seoul; Kwang Hyuk Lee, Yongin; Youn Ha Lee, Kyungkee-do; Young Gi Kim, Seoul, all of (KR)

(73) Assignee: Cheil Jedang Corporation, Seoul (KR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/931,306

(22) Filed: Sep. 16, 1997

(30) Foreign Application Priority Data

Nov. 28, 1996 (KR) .................................. 96-58702

(51) Int. Cl.[7] ....................... C07D 401/12; C07D 403/12
(52) U.S. Cl. ..................... 544/326; 544/327; 544/328; 544/329; 544/295; 544/296; 544/322
(58) Field of Search ................... 544/322, 326, 544/327, 295, 296, 328, 329; 514/256

(56) References Cited

U.S. PATENT DOCUMENTS 5,474,996 * 12/1995 Caille et al. ..................... 514/256

OTHER PUBLICATIONS

Robins et al., J. Am. Chem. Soc. 75 (1953) 263–266, 1953.*

* cited by examiner

*Primary Examiner*—John M. Ford
(74) *Attorney, Agent, or Firm*—Burns, Doane, Swecker & Mathis, L.L.P.

(57) ABSTRACT

Novel 4,5-diamino pyrimidine derivatives are described by the following general formula I:

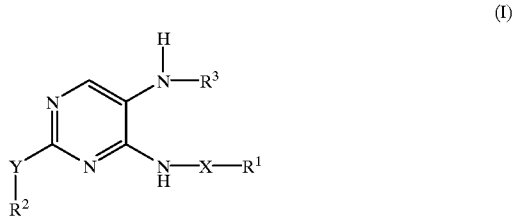

in which X is a direct bond, $C_{1-4}$ alkylene, $C_{1-4}$ alkyleneoxy, $C_{1-4}$ alkoxyphenyl or phenyl $C_{1-4}$ alkylene; Y is a direct bond or $C_{1-2}$ alkyl, $R^1$ is (i) 5–15 membered cyclic or fused heterocompound which includes one or two atoms selected from a group consisting of nitrogen, oxygen and sulfur and which is substituted with one or two substituents selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy, $R^2$ is 5–15 membered cyclic or fused heterocompound which includes one or two nitrogen atoms and, optionally, one oxygen or sulfur atom, and which is substituted with one or two substituents selected from a group consisting of hydrogen, hydroxy, halogen, nitro, hydroxy $C_{1-5}$ alkyl, $C_{1-6}$ alkyl, $C_{3-6}$ alkenyl and halogen $C_{1-4}$ alkoxy; $R^3$ is hydrogen,

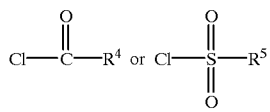

in which $R^4$ and $R_5$ are each independently selected from a group consisting of hydroxy, $C_{1-6}$ alkyl, $C_{3-7}$ cycloalkyl, $C_{3-6}$ alkenyl, halogen $C_{1-6}$ alkyl, halogen $C_{2-6}$ alkenyl and $C_{1-4}$ alkoxy or $R^4$ and $R^5$ represent each independently

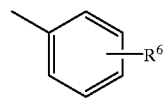

in which $R^6$ is selected from a group consisting of hydrogen, hydroxy, $C_{1-6}$ alkyl, $C_{3-6}$ alkenyl, halogen $C_{1-6}$ alkyl, halogen, nitro and $C_{1-4}$ alkoxy.

9 Claims, No Drawings

4,5-DIAMINOPYRIMIDINE DERIVATIVES AND A METHOD FOR THE PREPARATION THEREOF

FIELD OF THE INVENTION

The present invention relates to novel 4,5-diaminopyrimidine derivatives useful in prevention or treatment of diseases implicated in respiratory system by inhibiting cyclic guanosine 3',5'-monophosphate phosphodiesterase. In addition, the present invention relates to a process for producing the said compounds.

BACKGROUND OF THE INVENTION

It is known that cyclic guanosine 3',5'-monophosphate (cGMP) induces an relaxation of cardiac muscle or smooth muscle and is implicated in the cellular growth of lymphocyte. However, there are reports in which cGMP is converted into inactive 5'GMP by cGMP phosphodiesterase, so the action of cGMP is lost. Therefore, compounds having inhibitory activity of cGMP phosphodiesterase will be able to maintain or increase level of cGMP and so will act as keeping a symmetrical metabolism. As such, the compounds can be effectively used in the prevention or treatment of hypertension, cardiagra, arteriosclerosis, respiratory system disease such as chronic bronchial asthma or bronchitis, etc.

U.S. Pat. No. 5,318,975 describes, as inhibitor of cGMP phosphodiesterase, 5-aminopyrimidine derivatives compounds of the following formula A:

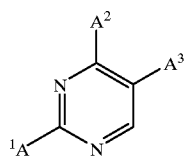

wherein $A^1$ represents hydrogen or imidazole substituted with lower alkyl, $A^2$ represents hydrogen or lower alkyl and $A^3$ represents imidazolecarboxylamide substituted with lower alkyl.

EP 640,599 describes, as inhibitor of cGMP phosphodiesterase, 4-aminopyrimidine derivatives compound of the following formula B:

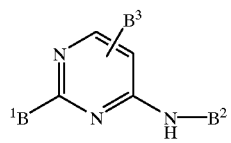

wherein $B^1$ represents 4–15 membered heterocyclic ring substituted with lower alkyl, lower alkoxy, halogen, etc., $B^2$ represents 4–15 membered heterocyclic ring substituted with lower alkyl, lower alkoxy, halogen, nitro, ester, etc. or hydroxy(lower alkoxy), B represents 4–15 membered heterocyclic ring substituted with lower alkyl, lower alkoxy, halogen, nitro, sulfone, etc.

DETAILED DESCRIPTION OF THE INVENTION

In one aspect, the present invention provides novel 4,5-diaminopyrimidine derivatives or physiologically acceptable salts, solvates or metabolically readily convertible ester thereof which have the inhibitory activity of cGMP phosphodiesterase. The compounds are represented as the general formula (I):

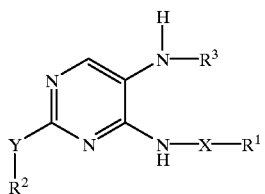

Formula I in which X is a direct bond, $C_{1-4}$ alkylene, $C_{1-4}$ alkyleneoxy, $C_{1-4}$ alkoxyphenyl or phenyl $C_{1-4}$ alkylene; Y is a direct bond or $C_{1-2}$ alkyl; $R^1$ is (i) 5–15 membered cyclic or branched chain heterocompound which includes one or two atoms selected from a group consisting of nitrogen, oxygen and sulfur and which is substituted with one or two substituent selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy; $R^2$ is 5–15 membered cyclic or branched chain heterocompound which includes one or two atoms selected from a group consisting of nitrogen, oxygen and sulfur and which is substituted with one or two substituent selected from a group consisting of hydrogen, hydroxy, halogen, nitro, hydroxy $C_{1-5}$ alkyl, $C_{1-6}$ alkyl, $C_{3-6}$ alkenyl and halogen $C_{1-4}$ alkoxy; $R^3$ is hydrogen,

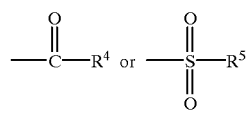

in which $R^4$ and $R^5$ are each independently selected from a group consisting of hydroxy, $C_{1-6}$ alkyl, $C_{3-7}$ cycloalkyl, $C_{3-6}$ alkenyl, halogen $C_{1-6}$ alkyl, halogen $C_{2-6}$ alkenyl and $C_{1-4}$ alkoxy or $R^4$ and $R^5$ represent each independently

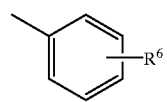

in which $R^6$ is selected from a group consisting of hydrogen, hydroxy, $C_{1-6}$ alkyl, $C_{3-6}$ alkenyl, halogen $C_{1-6}$ alkyl, halogen, nitro and $C_{1-4}$alkoxy.

The compound of the general formula I may be in the form of optical isomer or geometrical isomer. These isomers are included in the present invention.

The present invention provides a process for producing the compound of the general formula I which comprises (a) reacting a compound of the following structure III:

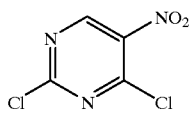

(III)

with a compound of the general formula III-a:

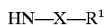 HN—X—R$^1$ (III-a)

in which X and $R^1$ represent the same as defined above, to give a compound of the general formula IV:

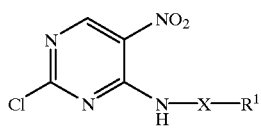
(IV)

in which X and $R^1$ represent the same as defined above, (b) reacting the compound IV with a compound of the general formula IV-a:

Y—$R^2$ (IV-a)

in which Y and $R^2$ represent the same as defined above, to give a compound of the general formula V:

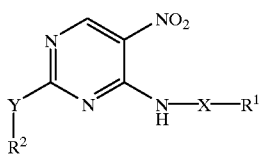
(V)

in which X, $R^1$ and $R^2$ represent the same as defined above, (c) reducing the compound V to give a compound of the general formula VI:

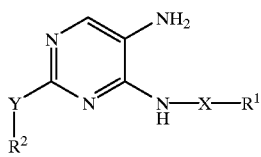
(VI)

in which X, Y, $R^1$, and $R^2$ represent the same as defined above, (d-i) reacting the compound VI with a compound of the general formula (VI-1):

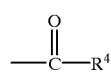
(VI-1)

in which $R^4$ is selected from a group consisting of hydroxy, $C_{1-6}$ alkyl, $C_{3-7}$ cycloalkyl, $C_{3-6}$ alkenyl, halogen $C_{1-6}$ alkyl, halogen $C_{2-6}$ alkenyl and $C_{1-4}$ alkoxy or $R^4$ represents

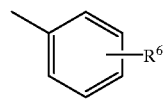

in which $R^6$ is selected from a group consisting of hydrogen, hydroxy, $C_{1-6}$ alkyl, $C_{3-6}$ alkenyl, halogen $C_{1-6}$ alkyl, halogen, nitro and $C_{1-4}$ alkoxy to give the compound of the general formual I-A:

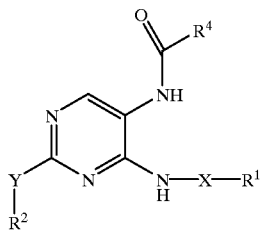
(I-A)

in which X, Y, $R^1$, $R^2$ and $R^4$ are the same as defined above; or (d-ii) reacting the compound VI with a compound of the general formula (VI-2):

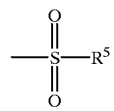
(VI-2)

in which $R^5$ is selected from a group consisting of hydroxy, $C_{1-6}$ alkyl, $C_{3-7}$ cycloalkyl, $C_{3-6}$ alkenyl, halogen $C_{1-6}$ alkyl, halogen $C_{2-6}$ alkenyl and $C_{1-4}$ alkoxy or $R^5$ represents

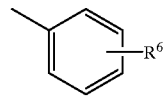

in which $R^6$ is selected from a group consisting of hydrogen, hydroxy, $C_{1-6}$ alkyl, $C_{3-6}$ alkenyl, halogen $C_{1-6}$ alkyl, halogen, nitro and $C_{1-4}$ alkoxy, to give the compound of the general formula I-B:

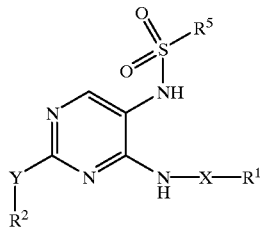
(I-B)

in which X, Y, $R^1$, $R^2$ and $R^5$ are the same as defined above.

The compound III is described in WO 9510506 and, preferably, can be prepared by reacting the compound II with phosphorus oxychloride in the presence of a base. N,N-diethyl-aniline, N,N-dimethylaniline or N,N-diisopropylethylamine can be used as the base. As such, the reaction is carried out at a reflux temperature.

The compound IV can be prepared by reacting the compound III with the compound of the formula III-a: HN—X—$R^1$ in which $R^1$ is the same as defined above, preferably, using pyridine or triethylamine in solvent such as dichloromethane or acetonitrile at 0° C. to room temperature (J. Med. Chem. 1994, 37, 2106).

The compound V can be prepared by dissolving the compound IV in a polar solvent and reacting the solution with the compound of the formula IV-a: Y—$R^2$ in which $R^2$ is the same as defined above, at 0° C. to reflux temperature. Usually, the compound V is obtained as crystals in acetonitrile, ethanol or isopropanol.

The compound VI is obtained by reacting the compound V with iron and acid in polar solvent under reflux (WO 9518097) or by reacting the compound V with sodium borohydride and 5% palladium on activated carbon in solvent such as methanol or ethanol at 0° C. to 25° C. (*Synthesis*, 1994, 1437).

The compound I-A is produced by reacting the compound VI with the compound VI-1:

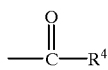

in which $R^4$ is the same as defined above, using pyridine, triethylamine or N,N-diisopropylethylamine as a base in solvent such as acetonitrile, dichloromethane or tetrahydrofurane at 0° C. to reflux temperature.

The compound I-B is produced by reacting the compound VI with the compound VI-2:

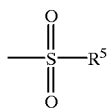

in which $R^5$ is the same as defined above, using pyridine or N,N-diisopropylethylamine as a base in solvent such as acetonitrile, dichloromethane or tetrahydrofurane at 0° C. to 25° C.

The invention will now be described with reference to the following illustrative Examples.

EXAMPLES

Reference Example 1

2,4-dichloro-5-nitropyrimidine 25 g of 5-nitrourasil was suspended in 490 ml of phosphorous oxychloride for 10 minutes and diisopropylethylamine was slowly added to the suspension at room temperature. The reaction suspension was refluxed at 130° C. for 3 hours. The solution was concentrated under reduced pressure to be a volume of 100 ml. Then, the solution was added dropwise to 500 ml of ice water and stirred for 1 hour, and extracted with diethyl ether (300 ml×5). The organic layer was washed with 500 ml of saturated ammonium chloride and dried over anhydrous magnesium sulfate and concentrated under reduced pressure. Column chromatography on silica gel (ethyl acetate:hexane=1:5) afforded 16.8 g of the title compound.

NMR (CDCL$_3$, 400 MHz): δ=8.82(1H,s)

Reference Example 2

4N-benzyl-2-chloro-5-nitropyrimidineamine 2.7 ml of benzylamine was added to a solution of 5.0 g of the 2,4-dichloro-5-nitropyrimidine (Reference Example 1) in 75 ml of dichloromethane at 5° C. and the solution was stirred for 1 hour. 3.6 ml of triethylamine was added to the solution at 5° C., stirred for 10 minutes, washed with 150 ml of saturated sodium bicarbonate, dried over anhydrous magnesium sulfate, and concentrated under reduced pressure to obtain 6.6 g of the title compound.

NMR(CDCl$_3$, 400 MHz): δ=4.68(2H, d), 7.17(5H, m), 8.65(1H, t), 8.84(1H, s)

Reference Example 3

4N-(4-bromobenzyl)-2-chloro-5-nitropyrimidineamine 2,4-dichloro-5-nitropyrimidine obtained by Reference Example 1 was used as a starting material and was reacted in the same manner as Reference Example 2 to obtain the title compound.

NMR (CDCl$_3$, 400 MHz): δ=4.81(2H, d), 7.32(2H, d), 7.45(2H, d), 8.61(1H, t), 8.85(1H, s)

Reference Example 4

2-chloro-4N-(2-chlorobenzyl)-5-nitropyrimidineamine 2,4-dichloro-5-nitropyrimidine obtained by Reference Example 1 was used as a starting material and was reacted in the same manner as Reference Example 2 to obtain the title compound.

NMR (CDCl$_3$, 400 MHz): δ=4.75(2H, d), 7.43(3H, d), 7.48(1H, d), 8.61(1H, t), 8.85(1H, s)

Reference Example 5

2-chloro-4N-(1,3-dioxaindan-5-yl)methyl-5-nitropyrimidineamine 3.0 ml of piperonylamine was added to a solution of 5.0 g of 2,4-dichloro-5-nitropyrimidine obtained by Reference Example 1 in 75 ml of dichloromethane at 5° C. and the solution was stirred for 1 hour. 3.6 ml of triethylamine was then added to the reaction solution at 5° C., stirred for 10 minutes, washed with saturated sodium bicarbonate, dried over anhydrous magnesium sulfurate, and concentrated under reduced pressure to obtain 6.9 g of the title compound.

NMR(CDCl$_3$, 400 MHz): δ=4.60(2H, d), 5.95(2H, s), 6.86(1H, d), 6.91(1H, d), 7.03(1H, d), 8.61(1H, t), 8.85(1H, s).

Reference Example 6

Ethyl 1-(4-benzylamino-5-nitropyrimidin-2-yl)-4-piperidinecarboxylate 3.5 ml of isonipecotate was added to a solution of 1.0 g of 4N-benzyl-2-chloro-5-nitropyrimidineamine (Reference Example 2) in 35 ml of acetonitrile and the suspension was stirred overnight. 35 ml of ethanol was added to the suspension, cooled to 5° C. and stirred for 1 hour. Filtration afforded 0.91 g of the yellowish title compound.

NMR(CDCl$_3$, 400 MHz): δ=1.06(3H, t), 1.51(2H, m), 1.79(2H, ABq), 2.39(1H, m), 2.97(2H, m), 3.95(2H, q), 4.40(2H, d), 4.54(2H, d), 7.15(5H, m), 8.54 (1H, t), 8.82(1H, s).

Reference Example 7

4N-benzyl-2-(4-ethylpiperazino)-5-nitro-4-pyrimidineamine 4N-benzyl-2-chloro-5-nitropyrimidineamine (Reference Example 2) was used as a starting material and was reacted in the same manner as Reference Example 6 to obtain the title compound.

NMR(CDCl$_3$, 400 MHz): δ=0.93(3H, t), 2.25(6H, m), 3.79(4H, m), 4.55(2H, d), 7.16(5H, m), 8.58(1H, t), 8.81 (1H, s)

Reference Example 8

4N-(4-bromobenzyl)-2-(1H-imidazol-1-yl)-5-nitropyrimidineamine 4N-(4-bromobenzyl)-2-chloro-5-nitropyrimidineamine (Reference Example 3) was used as a starting material and was reacted in the same manner as Reference Example 6 to obtain the title compound.

NMR(DMSO-$d_6$, 400 MHz): δ=4.81(2H, d), 7.07(1H, s), 7.32(2H, d), 7.45(2H, d), 7.79(1H, t), 8.47(1H, s), 9.16(1H, s), 9.67(1H, t)

Reference Example 9

Ethyl 1-[4-(1,3-dioxaindan-5-yl)methylamino-5-nitropyrimidin-2-yl]-4-piperidinecarboxylate 3.0 ml of ethyl isonipecotate was added to a solution of 1.0 g of 2-chloro-4N-(1,3-dioxaindane-5-yl)methyl-5-nitropyrimidineamine (Reference Example 5) in 45 ml of acetonitrile at room temperature and the suspension was stirred overnight. 45 ml of ethanol was added to the suspension, cooled to 5° C., and stirred for 1 hour. Filtration afforded 1.0 g of the yellowish title compound.

NMR (CDCl$_3$, 400 MHz): δ=1.26(3H, t), 1.71(2H, m), 1.97(2H, ABq), 2.58 (1H, m), 3.18(2H, m), 4.15(2H, q), 4.52(2H, m), 4.67(2H, d), 5.94(2H, s), 6.78(3H, m), 8.63 (1H, t), 8.98(1H, s)

Reference Example 10

4N-(1,3-dioxaindan-5-yl)methyl-2-(2-ethyl-4-methyl-1H-imidazol-1-yl)-5-nitropyrimidineamine The compound prepared by Reference Example 5 was used as a starting material and was reacted in the same manner as Reference Example 9 to obtain the title compound.

NMR (CDCl$_3$, 400 MHz): δ=1.31(3H, t), 2.24(3H, s), 3.22(2H, q), 4.78(2H, d), 6.00(2H, s), 6.94(3H, m), 7.58(1H, s), 8.72(1H, t), 9.25(1H, s)

Reference Example 11

Ethyl 1-[4-(1,3-dioxaindan-5-yl)methylamino-5-nitropyrimidin-2-yl)-4-piperazine carboxylate 2.5 ml of ethyl 1-piperazinecarboxylate was added to a solution of 1.75 g of 2-chloro-4N-(1,3-dioxaindan-5-yl)methyl-5-nitropyrimidineamine (Reference Example 5) in 60 ml of acetonitrile and the suspension was stirred overnight. 100 ml of ethanol was added to the suspension, cooled to 5° C., and stirred for 1.5 hour. Filtration afforded 2.1 g of the title compound.

NMR (CDCl$_3$, 400 MHz): δ=1.55(3H, t), 3.77(4H, d), 4.01(4H, d), 4.48(2H, q), 4.77(2H, d), 6.10(2H, s), 7.00(2H, d), 7.04(1H, s), 8.25(1H, t), 9.11(1H, s)

Reference Example 12

4N-(1,3-dioxaindan-5-yl)methyl-2-(1H-imidazol-1-yl)-5-nitropyrimidineamine 2.3 g of 1H-imidazole was added to a solution of 1.75 g of 2-chloro-4N-(1,3-dioxaindan-5-yl)methyl-5-nitropyrimidineamine (Reference Example 5) in 60 ml of acetonitrile and the suspension was stirred overnight. The suspension was concentrated under reduced pressure to obtain solid. The resulting solid was suspended in water:ethanol=40 ml:100 ml, filtered, and dried to obtain 1.55 g of the title compound.

NMR (CDCl$_3$, 400 MHz): δ=4.72(2H, d), 6.09(2H, s), 6.98(2H, d), 7.03(1H, s), 7.13(1H, s), 7.80(1H, s), 8.35(1H, t), 8.40(1H, s), 9.18(1H, s)

Reference Example 13

4N-benzyl-5-nitro-2-(1H-tetrazol-1-yl)pyrimidineamine 4.0 g of 4N-benzyl-2-chloro-5-nitropyrimidineamine (Reference Example 2) was added to a solution of 3.0 g of 1H-tetrazole in 120 ml of acetonitrile. A mixture of 2.5 ml of triethylamine and 45 ml of acetonitrile was added dropwise to the solution. The reaction solution was stirred overnight and was cencentrated under reduced pressure to obtain solid. The resulting solid was suspended in 3N sodium hydroxide solution for 1 hour, filtered and dried to obtain 3.80 g of the title compound.

NMR (CDCl$_3$, 400 MHz): δ=4.99(2H, d), 7.44(5H, m), 8.79(1H, t), 9.32(1H, s), 9.48(1H, s)

Reference Example 14

Ethyl 1-(5-amino-4-benzylaminopyrimidin-2-yl)-4-piperidinecarboxylate 1.3 ml of acetic acid, 1.3 ml of distilled water and 1.40 g of iron were added to a suspension of 0.90 g of ethyl 1-[4-benzylamino-5-nitropyrimidin-2-yl)-4-piperidinecarboxylate (Reference Example 6) in 50 ml of ethanol and the reaction solution was refluxed for 5 hours. The dark blue solution was filtered to remove the insoluble substance, and concentrated under reduced pressure to obtain the thin yellow oily product. The resulting product was dissolved in dichloromethane and washed with 10% sodium carbonate(50 ml×2). The organic layer was dried over anhydrous magnesium sulfate and concentrated under reduced pressure to obtain 0.57 g of the title compound as a oily product.

NMR DMSO-$d_6$, 400 MHz): δ=1.04(3H, t), 1.45(2H, m), 1.76(2H, m), 2.41(1H, m), 2.91(2H, m), 3.93(2H, q), 4.40 (2H, d), 4.48(2H, d), 5.31(2H, s), 7.20(5H, m), 7.54(1H, t), 7.62(1H, s).

Reference Example 15

4N-benzyl-2-(4-ethylpiperazino)-5-pyrimidinediamine 4N-benzyl-2-(4ethylpiperazino)-5-nitro-4-pyrimidineamine (Reference Example 7) was used as a starting material and was reacted in the same manner as Reference Example 14 to obtain the title compound.

NMR (CDCl$_3$, 400 MHz): δ=0.92(3H, t), 2.23(6H, m), 3.75(4H, m), 4.48(2H, d), 5.31(2H, s), 7.15(5H, m), 7.38 (1H, t), 7.60(1H, s).

Reference Example 16

4N-(4-bromobenzyl)-2-(1H-imidazol-1-yl)-5-pyrimidinediamine

The compound prepared by Reference Example 8 was used as a starting material and was reacted in the same manner as Reference Example 14 to obtain the title compound.

NMR (DMSO-$d_6$, 400 MHz): δ=4.65(2H, D), 5.40(2H, s), 7.07(1H, s), 7.28(2H, d), 7.33(1H, t), 7.43(2H, d), 7.58(1H, s), 7.62(1H, s), 8.47(1H, s).

Reference Example 17

Ethyl 1-[5-amino-4-(1,3-dioxaindan-5-yl)
methylamino]pyrimidin-2-yl]-4-
piperidinecarboxylate 5.0 ml of acetic acid, 4.1 ml of distilled water and 4.1 g of iron were added to a suspension of 2.00 g of the compound prepared by Reference Example 9 in 120 ml of ethanol and the suspension was refluxed for 3 hours. The dark blue suspension was filtered to remove the insoluble substance, and concentrated under reduced pressure to obtain the thin yellowish oily product. The resulting product was dissolved in dichloromethane and washed with 10% sodium carbonate(100 ml×2). The organic layer was dried over anhydrous magnesium sulfate, and concentrated under reduced pressure to yield 1.21 g of the thin yellow title compound.

NMR (DMSO-$d_6$, 400 MHz): $\delta$=1.23(3H, t), 1.69(2H, m), 1.95(2H, q), 2.5 6(1H, m), 3.17(2H, m), 4.12(2H, q), 4.50 (2H, m), 4.67(2H, d), 5.43(2H, s), 5.96(2H, m), 6.76(3H, m), 7.58(1H, t), 7.65(1H, s).

Reference Example 18

4N-(1,3-dioxaindan-5-yl)methyl-2-(2-ethyl-4-
methyl-1H-imidazol-1-yl)-5-pyrimidinediamine The compound prepared by Reference Example 10 was used as a starting material and was reacted in the same manner as Reference Example 14 to obtain the title compound.

NMR (DMSO-$d_6$, 400 MHz): $\delta$=1.20(3H, t), 2.27(3H, s), 3.17(2H, q), 4.55(2H, d), 5.33(2H, s), 5.98(2H, s), 6.86(2H, q), 6.93(1H, s), 7.60(1H, s), 7.77(1H, s), 7.93(1H, t).

Reference Example 19

Ethyl 1-[5-amino-4-(1,3-dioxaindan-5-yl)
methylaminopyrimidin-2-yl]-4-
piperazinecarboxylate 10.0 ml of acetic acid, 5.0 ml of distilled water and 4.01 g of iron were added to a suspension of 3.00 g of the compound prepared by Reference Example 11 in 150 ml of ethanol and the suspension was refluxed for 3 hours. The dark blue suspension was filtered to remove the insoluble substance, and concentrated under reduced pressure to obtain the thin yellow oily product. The resulting product was dissolved in dichloromethane and washed with 10% sodium carbonate(150 ml×2). The organic layer was dried over anhydrous magnesium sulfate, and concentrated under reduced pressure. Column chromatography on silica gel (methanol:dichloromethane=1:10) afforded 2.0 g of the title compound as a thin yellow solid.

NMR (DMSO-$d_6$, 400 MHz): $\delta$=1.52(3H, t), 3.75(4H, d), 4.00(4H, d), 4.46(2H, q), 4.70(2H, d), 5.38(2H, s), 6.08(2H, s), 6.97(2H, d), 7.02(1H, s), 7.45(1H, t), 7.65(1H, s)

Reference Example 20

4N-(1,3-dioxaindan-5-yl)methyl-2-(1H-imidazol-1-
yl)-5-pyrimidinediamine

The compound prepared by Reference Example 12 was used as a starting material and was reacted in the same manner as Reference Example 14 to obtain the title compound.

NMR (DMSO-$d_6$, 400 MHz): $\delta$=4.68(2H, d), 5.38(2H, s), 6.05(2H, s), 6.97(2H, d), 7.02(1H, s), 7.13(1H, s), 7.46(1H, t), 7.67(1H, s), 7.80(1H, s), 8.37(1H, s)

Reference Example 21

4N-benzyl-2-(1H-tetrazol-1-yl)-5-pyrimidinediamine

The compound prepared by Reference Example 13 was used as a starting material and was reacted in the same manner as Reference Example 14 to obtain the title compound.

NMR (DMSO-$d_6$, 400MHz): $\delta$=4.72(2H, d), 5.36(2H, s), 7.28(1H, t), 7.34(2H, t), 7.43(2H, t), 7.63(1H, s), 7.65(1H, t), 9.94(1H, s)

Example 1

1-[4-benzylamino-5-(2-bromophenylsulfonamido)
pyrimidin-2-yl]-4-piperidinecarboxylic acid 230 mg of 2-bromobenzenesulfonyl chloride was added to a solution of 400 mg of the compound prepared by the Reference Example 14 in 40 ml of ethanol at room temperature and the solution was stirred for 10 minutes. 0.27 ml of pyridine was added to the yellow reaction solution, stirred at room temperature overnight, and concentrated under reduced pressure to remove the solvent. The oily product obtained therefrom was mixed with 50 ml of dichloromethane and washed with saturated sodium carbonate. The organic layer was dried over anhydrous magnesium sulfate and concentrated under reduced pressure. Column chromatography on silica gel (ethyl acetate:hexane=1:1) afforded 170 mg of the pink solid ester compound.

150 mg of the ester compound was dissolved in 30 ml of methanol. 15 ml of 1.5N sodium hydroxide was added to the solution and stirred for 30 minutes at room temperature. The reaction solution was concentrated under reduced pressure to remove the organic solvent. Then, the aqueous layer was adjusted to pH4.0 by using 3.0 N hydrochloric acid and stirred for 30 minutes. Filtration afforded 110 mg of the title compound as a white solid. m.p. 114–117° C.

NMR (DMSO-$d_6$, 400 MHz): $\delta$=1.28(2H, m), 1.71(2H, m), 2.40(1H, m), 2.81(2H, t), 4.30(2H, d), 4.46(2H, d), 7.01(1H, s), 7.21(1H, m), 7.27(5H, m), 7.52(2H,m), 7.89 (2H, m), 9.40(1H, s), 12.35(1H, s).

Example 2

1-[4-benzylamino-5-(4-bromophenylsulfonamido)
pyrimidin-2-yl]-4-piperidinecarboxylic acid 210 mg of 4-bromobenzenesulfonyl chloride was added to a solution of 300 mg of the compound prepared by the Reference Example 14 in 40 ml of dichloromethane at room temperature and the solution was stirred for 10 minutes. 0.20 ml of pyridine was added to the yellow reaction solution, stirred for 30 hours at room temperature, washed with 50 ml of saturated sodium carbonate, and the organic layer was dried over anhydrous magnesium sulfate and concentrated under reduced pressure. The oily resulting material was purified by column chromatography on silica gel (methanol:dichloromethane=7.5% v/v) to obtain 300 mg of the yellow solid ester compound.

250 mg of the ester compound was dissolved in 30 mg of ethanol. 15 ml of 1.5N sodium hydroxide was added to the solution and stirred for 3.5 hours at room temperature. The reaction solution was concentrated under reduced pressure to remove the organic solvent. Then, the aqueous layer was adjusted to pH 4.0 by using 3.0 N hydrochloric acid and stirred for 1 hour at 5° C. Filtration afforded 110 mg of the title compound as a white solid. m.p. 136–138° C.

NMR (DMSO-d$_6$, 400 MHz): δ=1.36(2H, m), 1.76(2H, m), 2.45(1H, m), 2.91(2H, t), 4.25(2H, d), 4.40(2H, d), 7.11(1H, s), 7.23(5H, m), 7.53(1H, s), 7.70 (2H, d), 7.80(2H, d), 9.58(1H, s), 12.48(1H, brs).

Example 3

1-[4-benzylamino-5-(4-methylphenylsulfoneamido) pyrimidin-2-yl]-4-piperidinecarboxylic acid 180 mg of p-toluenesulfonyl chloride was added to a solution of 280 mg of the compound prepared by the Reference Example 14 in 40 ml of dichloromethane at room temperature and the solution was stirred for 10 minutes. 0.20 ml of pyridine was added to the yellow reaction solution, and stirred for 14 hours at room temperature. The solution was washed with 30 ml of 1.5 N sodium hydroxide, the organic layer was dried over anhydrous magnesium sulfate and concentrated under reduced pressure to obtain 450 mg of the yellow solid ester compound.

450 mg of the ester compound was dissolved in 50 mg of ethanol. 25 ml of 1.5 N sodium hydroxide was added to the solution and stirred for 2.5 hours at room temperature to complete the hydrolysis reaction. The reaction solution was concentrated under reduced pressure to remove the organic solvent. The aqueous layer was adjusted to pH 3.5 by using 3.0 N hydrochloric acid and stirred for 1 hour at 5° C. Filtration afforded 170 mg of the title compound as a white solid. m.p. 126–127° C.

NMR (DMSO-d$_6$, 400MHz): δ=1.31(2H, m), 1.72(2H, m), 2.39(3H, s), 2.41(1H, m), 2.82(2H, t), 4.31(2H, d), 4.40(2H, d), 7.02(1H, s), 7.10(1H, t), 7.28(5H, m), 7.38(2H, d), 7.63(2H, d), 9.04(1H, s), 12.20(1H, s)

Example 4

1-[4-benzylamino-5-(4-chlorophenylcarboxamido) pyrimidin-2-yl]-4-piperidinecarboxylic acid The compound prepared by Reference Example 14 and 4-chlorobenzoyl chloride were used as starting materials and were reacted in the same manner as in Example 3 to obtain the title compound. m.p. 155–157° C.

NMR (DMSO-d$_6$, 400 MHz): δ=1.48(2H, m), 1.85(2H, m), 2.56(1H, m), 3.14(2H, t), 4.29(2H, d), 4.58(2H, d), 7.23(1H, t), 7.35(5H, m), 7.50(2H, d), 7.80(1H, s), 8.06(2H, d), 9.99(1H, s), 12.39(1H, s).

Example 5

1-(4-benzylamino-5-hexylcarboxamidopyrimidin-2-yl)-4-piperidinecarboxylic acid

The compound prepared by Reference Example 14 and hexanoyl chloride were used as starting materials and were reacted in the same manner as Example 3 to obtain the title compound. m.p. 245° C. (decomposition)

NMR (DMSO-d$_6$, 400 MHz): δ=0.86(3H, t), 1.27(3H, m), 1.34(3H, m), 1.57 (2H, t), 1.64(2H, d), 2.00(1H, m), 2.27 (2H, t), 2.85(2H, t), 4.31(2H, d), 4.48(2H, d), 7.18(1H, t), 7.33(5H, m), 7.62(1H, s), 9.24(1H, s), 12.42(1H, s).

Example 6

1-(4-benzylamino-5-ethylsulfonamidopyrimidin-2-yl)-4-piperidinecarboxylic acid

The title compound was obtained according to the procedure of Example 3 by using the compound prepared by Reference Example 14 and ethanesulfonyl chloride as starting materials. m.p. 205° C.

NMR(DMSO-d$_6$, 400 MHz): δ=1.22(3H, t), 1.33(2H, m), 1.75(2H, m), 2.45(1H, m), 2.88(2H, t), 3.04(2H, q), 4.40 (2H, d), 4.49(2H, d), 7.21(1H, t), 7.30(5H, m), 7.66(1H, s), 8.54(1H, s), 12.22(1H, s).

Example 7

1-(4-benzylamino-5-trifluoromethylsulfonamidopyrimidin-2-yl)-4-piperidinecarboxylic acid 350 mg of the compound prepared by Reference Example 14 was dissolved in 40 ml of dichlormethane and the solution was cooled to −70° C. under nitrogen atmosphere. 0.27 ml of triethylamine and 0.20 ml of trifluoromethanesulfonic anhydride were added to the solution and stirred for 1.5 hour at −70° C. The reaction solution was warmed to room temperature and washed with 30 ml of 1.5 N sodium hydroxide. The organic layer was dried over anhydrous magnesium sulfate and concentrated under reduced pressure to obtain the oily product. Column chromatography over silica gel (methanol:dichloromethane=7.5% v/v) afforded 280 mg of ester compound.

250 mg of the ester compound was dissolved in 30 ml of ethanol. 15 ml of 1.5 N sodium hydroxide was added to the solution, and stirred under reflux for 3.5 hours. The reaction solution was concentrated under reduced pressure to remove the organic solvent. The aqueous layer was adjusted to pH 3.5 by using 3.0 N hydrochloric acid and was stirred for 1 hour at 5° C. Filtration afforded 160 mg of the title compound as a white solid. m.p. 160° C.

NMR (DMSO-d$_6$, 400 MHz): δ=1.37(2H, m), 1.78(2H, m), 2.43(1H, m), 2.90(2H, t), 4.42(2H, d), 4.48(2H, d), 7.24(1H, t), 7.38(5H, m), 7.70(1H, s), 9.21(1H, s), 12.40 (1H, brs).

Example 8

4-benzylamino-5-(2-bromophenylsulfonamido)-2-(4-ethylpiperazino)pyrimidine hydrochloride 120 mg of the pre-base of the title compound was prepared by using the compound obtained by the Reference Example 15 and 2-bromobenzenesulfonyl chloride as starting materials according to the procedure of Example 3 and was dissolved in 15 ml of methanol. 4 ml of 5% HCl-methanol was added to the solution and stirred for 30 minutes at room temperature. The reaction solution was concentrated under reduced pressure to remove the solvent. Crystallization with diethyl ether and petroleum ether afforded 95 mg of the title trihydrochloride compound. m.p. 67–70° C.

NMR (DMSO-d$_6$, 400 MHz): δ=1.18(3H, t), 2.50(6H, m), 3.79(4H, m), 4.69(2H, d), 6.12(1H, t), 7.30(5H, m), 7.40 (1H, s), 7.49(2H, q), 7.82(1H, q), 8.80(1H, q).

Example 9

4-benzylamino-5-(4-chlorophenylsulfonamido)-2-(4-ethylpiperazino)-pyrimidine hydrochloride 230 mg of the pre-base of the title compound was obtained by using the compound prepared by the Reference Example 15 and 4-chlorobenzenesulfonyl chloride as starting materials according to the procedure of Example 3 and was dissolved in 25 ml of methanol. 7 ml of 5% HCl-methanol was added to the solution and stirred for 30 minutes at room temperature. The reaction solution was concentrated under reduced pressure to remove the solvent. Crystallization with diethyl ether and petroleum ether afforded 180 mg of the title trihydrochloride compound. m.p. 78–81° C.

NMR (DMSO-$d_6$, 400 MHz): δ=0.98(3H, t), 2.28(6H, m), 3.38(4H, m), 4.43(2H, d), 6.59(1H, t), 7.23(5H, m), 7.33 (2H, q), 7.36(1H, s), 7.61(2H, q).

Example 10

5-(4-chlorophenylsulfonamido)-4-(4-bromobenzylamino)-2-(1H-imidazol-1-yl)pyrimidine 150 mg of 4-chlorobenzenesulfonyl chloride was added to a solution of 220 mg of the compound prepared by the Reference Example 16 in 40 ml of dichloromethane at room temperature and stirred for 10 minutes. 0.13 ml of pyridine was added to the reaction solution, stirred for 30 minutes at room temperature ans washed with 40 ml of 1.5 N sodium hydroxide. The organic layer was washed with 1N hydrochloric acid to remove the impure substance. The organic layer was dried over anhydrous magnesium sulfate and concentrated under reduced pressure to obtain thin yellow oily product. Crystallization with diethyl ether and petroleum ether afforded 186 mg of the title compound. m.p. 183–185° C.

NMR (DMSO-$d_6$, 400 MHz): δ=4.72(2H, d), 7.40(2H, d), 7.53(2H, d), 7.59(1H, s), 7.66(2H, d), 7.76(2H, d), 7.78(1H, t), 8.13(1H, t), 8.19(1H, d), 8.24(1H, d), 9.24(1H, s).

Example 11

Ethyl 1-[5-(2-bromophenylsulfonamido)-4-(1,3-dioxaindan-5-yl)methylaminopyrimidin-2-yl)-4-piperidinecarboxylate 180 mg of 2-bromobenzenesulfonyl chloride was added to a solution of 310 mg of the compound prepared by the Reference Example 17 in 50 ml of ethanol at room temperature and stirred for 10 minutes. The yellowish reaction solution was further stirred for 55 hours at room temperature and concentrated under reduced pressure to remove the solvent. The oily product obtained therefrom was mixed with 70 ml of chloroform and washed with saturated sodium carbonate(100 ml×2). The organic layer was dried over anhydrous magnesium sulfate and was concentrated under reduced pressure to obtain oily product. Column chromatography on silica gel (ethyl acetate:hexane=1:1) afforded 290 mg of the title compound as a solid. m.p. 160–161° C.

NMR(CDCl$_3$, 400 MHz): δ=1.17(3H, t), 1.57(2H, m), 1.80(2H, ABq), 2.41(1H, m), 2.85(2H, m), 4.05(2H, q), 4.40(2H, t), 4.44(2H, d), 5.88(2H, s), 5.90(1H, t), 6.71(3H, m), 7.15(1H, s), 7.35(2H, m), 7.68(1H, m), 7.83(1H, m).

Example 12

1-[5-(4-chloropenylsulfonamido)-4-(1,3-dioxaindan-5-yl)methylaminopyrimidin-2-yl)-4-piperidinecarboxylic acid 140 mg of 4-chlorobenzenesulfonyl chloride was added to a solution of 260 mg of the compound prepared by the Reference Example 17 in 40 ml of dichloromethane at room temperature and stirred for 10 minutes. 0.15 ml of pyridine was added to the reaction solution, and stirred for 45 hours at room temperature and washed with 30 ml of 1.5 N sodium hydroxide. The organic layer was dried over anhydrous magnesium sulfate and concentrated under reduced pressure to obtain 250 mg of the ester compound as a yellow solid.

250 mg of the ester compound was dissolved in 30 ml of ethanol. 15 ml of 1.5 N sodium hydroxide was added to the solution and stirred for 30 minutes at room temperature. The reaction solution was concentrated under reduced pressure to remove the organic layer. The aqueous layer was adjusted to pH 4.5 by using 3.0 N hydrochloric acid and stirred for 1 hour at 5° C. Filtration afforded 85 mg of the title compound as a white solid. m.p. 209–210° C.

NMR(DMSO-$d_6$, 400 MHz): δ=1.49(2H, m), 1.89(2H, m), 2.69(1H, m), 3.14(2H, m), 4.19(2H, brs), 4.41(2H, d), 6.00(2H, s), 6.72(1H, d), 6.83(1H, d), 6.85 (1H, d), 6.97(1H, s), 7.67(2H, m), 7.83(2H, m), 8.90(1H, brs), 9.96(1H, brs).

Example 13

5-(2-chloropenylcarboxamido)-4-(1,3-dioxaindan-5-yl)methylamino-2-(1H-2-ethyl-4-methylimidazol-1-yl)pyrimidine The title compound was obtained according to the procedure of Example 10 by using the compound prepared by Reference Example 18 and 2-chlorobenzoyl chloride as starting materials. m.p.: 152–154° C.

NMR (DMSO-$d_6$, 400 MHz): δ=1.24(3H, t), 2.30(3H, d), 3.27(2H, q), 4.60(2H, d), 5.97(2H, s), 6.87(2H, d), 6.99(1H, s), 7.54(3H, M), 7.82(1H, q), 7.92(1H, d), 8.33(1H, t), 8.50(1H, s), 10.29(1H, s).

Example 14

5-(2,4-dinitropenylcarboxamido)-4-(1,3-dioxaindan-5-yl)methylamino-2-(1H-2-ethyl-4-methylimidazol-1-yl)pyrimidine The title compound was obtained according to the procedure of Example 10 by using the compound prepared by Reference Example 18 and 2,4-dinitrobenzoyl chloride as starting matericals. m.p.: 170–171° C.

NMR (DMSO-$d_6$, 400 MHz): δ=1.27(3H, t), 2.32(3H, d), 3.34(2H, q), 4.60(2H, d), 5.98(2H, s), 6.90(2H, d), 6.98(1H, s), 8.32(1H, s), 8.45(1H, t), 8.52(1H, s), 9.22(2H, d), 10.27 (1H, s), 10.66(1H, s).

Example 15

Ethyl 1-]5-(4-bromophenylsulfonamido)-4-(1,3-dioxaindan-5-yl)methylaminopyrimidin-2-yl]-4-piperazinecarboxylate 180 mg of 4-bromobenzenesulfonyl chloride was added to a solution of 250 mg of the compound prepared by the Reference Example 19 in 40 ml of dichloromethane at room temperature and stirred for 10 minutes. 0.15 ml of pyridine was added to the yellow reaction solution, and stirred for 30 hours at room temperature and washed with 50 ml of 1.5 N sodium hydroxide. The organic layer was dried over anhydrous magnesium sulfate and concentrated under reduced pressure to obtain oily product. The residue was purified by column chromatography on silica gel (methanol:dichloromethane=7.5% v/v). Crystallization with diethyl ether and petroleum ether afforded 165 mg of the title compound. m.p. 173–176° C.

NMR (CDCl$_3$, 400 MHz): δ=1.52(3H, t), 3.73(4H, d), 3.96(4H, d), 4.40(2H, q), 4.75(2H, d), 6.18(1H, t), 6.21(2H, s), 7.02(2H, d), 7.06(1H, s), 7.51(1H, s), 7.89(4H, m), 8.05(1H, t), 8.45(1H, t), 9.11(1H, s).

Example 16

5-(4-chloropenylsulfonamido)-4-(1,3-dioxaindan-5-yl)methylamino-2-(1H-amidazol-1-yl)pyrimidine 140 mg of 4-chlorobenzenesulfonyl chloride was added to a solution of 210 mg of the compound prepared by the Reference Example 20 in 60 ml of dichloromethane at room temperature and stirred for 10 minutes. 0.15 ml of pyridine was added to the reaction solution, and stirred for 24 hours at room temperature and washed with 40 ml of 1.5 N sodium hydroxide. The organic layer was washed with 1N hydrochloric acid to remove the impure material. The organic layer was dried over anhydrous magnesium sulfate and concentrated under reduced pressure to obtain thin yellow oily product. Crystallization with diethyl ether and petroleum ether afforded 130 mg of the title compound. m.p. 206–207° C.

NMR (DMSO-$d_6$, 400 MHz): δ=4.45(2H, d), 5.97(2H, s), 6.76(1H, d), 6.83(1H, d), 6.89(1H, t), 7.05(1H, s), 7.47(1H, s), 7.65(2H, d), 7.74(2H, d), 7.76(1H, s), 7.97(1H, t), 8.40 (1H, s), 9.69(1H, s).

Example 17

5-ethylsulfoneamido-4-(1,3-dioxaindan-5-yl)methylamino-2-(1H-imidazol-1-yl)pyrimidine The title compound was obtained according to the procedure of Example 16 by using the compound prepared by Reference Example 20 and ethane-sulfonyl chloride as starting matericals. m.p.: 188–190° C.

NMR(DMSO-$d_6$, 400 MHz): δ=1.24(3H, t), 3.18(2H, q), 4.57(2H, d), 5.97(2H, s), 6.86(1H, d), 6.94(1H, d), 7.02(1H, d), 7.08(1H, q), 7.82(1H, t), 8.03(1H, s), 8.05(1H, t), 8.45 (1H, t), 9.11(1H, brs).

Example 18

5-hexylcarboxamido-4-(1,3-dioxaindan-5-yl)methylamino-2-(1H-imidazol-1-yl) pyrimidine The title compound was obtained according to the procedure of Example 16 by using the compound prepared by Reference Example 20 and hexanoyl chloride as starting materials. m.p. 148–150° C.

NMR(DMSO-$d_6$, 400 MHz): δ=0.90(3H, t), 1.14(4H, m), 1.60(2H, m), 2.35(2H, t), 4.56(2H, d), 5.96(2H, s), 6.86(1H, d), 6.91(1H, d), 7.03(1H, d), 7.07(1H, s), 7.81(1H, s), 7.83(1H, t), 8.09(1H, d), 8.32(1H, s), 9.22(1H, s).

Example 19

4-benzylamino-5-(4-bromophenylsulfonamido)-2-(1H-tetrazol-1-yl)pyrimidine 310 mg of 4-bromobenzenesulfonyl chloride was added to a solution of 270 mg of the compound prepared by the Reference Example 21 in 100 ml of acetonitrile at room temperature, and stirred for 10 minutes. 0.24 ml of pyridine was added to the solution, stirred for 40 hours at room temperature and concentrated under reduced pressure to remove acetonitrile. The residue was suspended in 30 ml of methanol, washed with 40 ml of 1.5 N sodium hydroxide, and filtered to obtain 186 mg of the title compound as a white solid. m.p. 184° C.

NMR (DMSO-$d_6$, 400 MHz): δ=4.58(2H, d), 7.31(5H, m), 7.71(2H, d), 7.76(1H, s), 7.78(2H, d), 8.38(1H, t), 9.97(1H, s), 10.06(1H, s).

Example 20

4-benzylamino-5-(2,4-dinitrophenylcarboxamido)-2-(1H-tetrazol-1-yl)pyrimidine 310 mg of dinitrobenzoyl chloride was added to a solution of 270 mg of the compound prepared by the Reference Example 21 in 100 ml of acetonitrile at room temperature and stirred for 10 minutes. 0.24 ml of pyridine was added to the solution, stirred for 40 hours at room temperature, and concentrated under reduced pressure to remove acetonitrile. The residue was suspended in 30 ml of methanol, washed with 40 ml of 1.5 N sodium hydroxide, and extracted with 50 ml of dichloromethane. The organic layer was washed with 50 ml of 1N hydrochloric acid to remove the impure material. The organic layer was dried over anhydrous magnesium sulfate and concentrated under reduced pressure to obtain 186 mg of the title compound as a white solid. m.p. 235° C. (decomposition)

NMR (DMSO-$d_6$, 400 MHz): δ=4.77(2H, d), 7.23(1H, t), 7.33(2H, t), 7.45(2H, d), 8.32(1H, s), 8.58(1H, t), 9.05(1H, s), 9.20(2H, d), 10.11(1H, s), 10.69(1H, s).

Example 21

4-benzylamino-5-(hexylcarboxamido)-2-(1H-tetrazol-1-yl)pyrimidine 310 mg of hexanoyl chloride was added to a solution of 270 mg of the compound prepared by the Reference Example 21 in 100 ml of acetonitrile at room temperature and stirred for 10 minutes. 0.24 ml of pyridine was added to the solution, stirred for 40 hours at room temperature, and concentrated under reduced pressure to remove acetonitrile. The residue was suspended in 30 ml of methanol, washed with 40 ml of 1.5 N sodium hydroxide, and extracted with 50 ml of dichlormethane. The organic layer was washed with 50 ml of 1N hydrochloric acid to remove the impure material. The organic layer was dried over anhydrous magnesium sulfate and concentrated under reduced pressure to obtain 186 mg of the title compound as a white solid. m.p. 144–145° C.

NMR (DMSO-$d_6$, 400 MHz): δ=0.89(3H, t), 1.31(4H, m), 1.59(2H, t), 2.38(2H, t), 4.46(2H, d), 7.25(1H, t), 7.33(2H, t), 7.45(2H, d), 8.10(1H, d), 8.34(1H, s), 9.35(1H, s), 10.06 (1H, s).

What is claimed is:

1. A compound of the formula I:

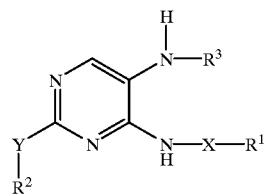

(I)

or physiologically acceptable salt thereof in which X is a direct bond, $C_{1-4}$ alkylene, $C_{1-4}$ alkyleneoxy, $C_{1-4}$ alkoxyphenyl or phenyl $C_{1-4}$ alkylene; Y is a direct bond or $C_{1-2}$ alkyl; $R^1$ is (i) 5–15 membered cyclic or fused heterocompound comprising 3–14 carbon atoms and one or two atoms selected from a group consisting of nitrogen, oxygen and sulfur, with the proviso that no oxygen-oxygen bond or sulphur-oxygen bond is formed, and which is substituted with one or two substituents selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy; $R^2$ is 5–15 membered cyclic or fused heterocompound comprising 3–14 carbon atoms and one or two nitrogen atoms and, optionally, one oxygen or sulfur atom, and which is substituted with one or two substituents selected from a group consisting of hydrogen, hydroxy, halogen, nitro, hydroxy $C_{1-5}$ alkyl, $C_{1-6}$ alkyl, $C_{3-6}$ alkenyl and halogen $C_{1-4}$ alkoxy; $R^3$ is hydrogen,

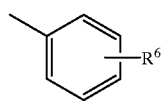

in which $R^4$ and $R^5$ are each independently selected from a group consisting of hydroxy, $C_{1-6}$ alkyl, $C_{3-7}$ cycloalkyl, $C_{3-6}$ alkenyl, halogen $C_{1-6}$ alkyl, halogen $C_{2-6}$ alkenyl and $C_{1-4}$ alkoxy or $R^4$ and $R^5$ represent each independently

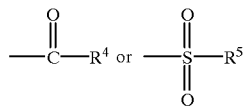

in which $R^6$ is selected from a group consisting of hydrogen, hydroxy, $C_{1-6}$ alkyl, $C_{3-6}$ alkenyl, halogen $C_{1-6}$ alkyl, halogen, nitro and $C_{1-4}$ alkoxy.

2. A process for producing a compound of the formula I-A:

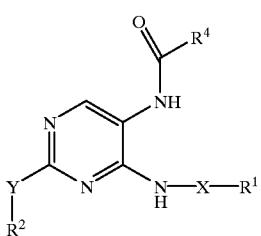

(I-A)

in which X is a direct bond, $C_{1-4}$ alkylene, $C_{1-4}$ alkyleneoxy, $C_{1-4}$ alkoxyphenyl or phenyl $C_{1-4}$ alkylene; Y is a direct bond or $C_{1-2}$ alkyl; $R^1$ is (i) 5–15 membered cyclic or fused heterocompound comprising 3–14 carbon atoms and one or two atoms selected from a group consisting of nitrogen, oxygen and sulfur, with the proviso that no oxygen-oxygen bond or sulphur-oxygen bond is formed, and which is substituted with one or two substituents selected from a group consisting of halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy; $R^2$ is 5–15 membered cyclic or fused heterocompound comprising 3–14 carbon atoms and one or two nitrogen atoms and, optionally, one oxygen or sulfur atom, and which is substituted with one or two substituents selected from a group consisting of hydrogen, hydroxy, halogen, nitro, hydroxy $C_{1-5}$ alkyl, $C_{1-6}$ alkyl, $C_{3-6}$ alkenyl and halogen $C_{1-4}$ alkoxy; $R^4$ is selected from a group consisting of hydroxy, $C_{1-6}$ alkyl, $C_{3-7}$ cycloalkyl, $C_{3-6}$ alkenyl, halogen $C_{1-6}$ alkyl, halogen $C_{2-6}$ alkenyl and $C_{1-4}$ alkoxy or $R^4$ represents

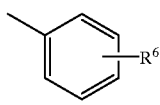

in which $R^6$ is selected from a group consisting of hydrogen, hydroxy, $C_{1-6}$ alkyl, $C_{3-6}$ alkenyl, halogen $C_{1-6}$ alkyl, halogen, nitro and $C_{1-4}$ alkoxy, which comprises:

(a) reacting a compound of the following structure III:

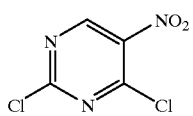

(III)

with a compound of the formula III-a:

$HN—X—R^1$ (III-a)

in which X and $R^1$ represent the same as defined above, to give a compound of the formula IV:

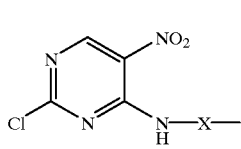

(IV)

in which X and $R^1$ represent the same as defined above, (b) reacting the compound IV with a compound of the formula IV-a:

$Y—R^2$ (IV-a)

in which Y and $R^2$ represent the same as defined above, to give a compound of the formula V:

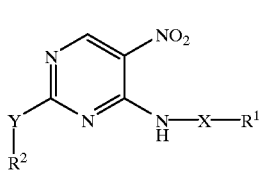

(V)

in which X, $R^1$ and $R^2$ represent the same as defined above, (c) reducing the compound V to give a compound of the formula VI:

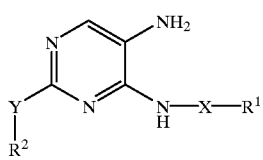

(VI)

in which X, Y, $R^1$, and $R^2$ represent the same as defined above, (d) reacting the compound VI with a compound of the formula VI-1:

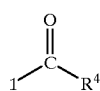
(VI-1)

in which R⁴ represents the same as defined above, to give the above compound I-A.

3. A process for producing a compound of the formula I-B:

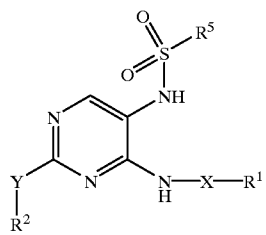
(I-B)

in which X is a direct bond $C_{1-4}$ alkylene, $C_{1-4}$ alkyleneoxy, $C_{1-4}$ alkoxyphenyl or phenyl, $C_{1-4}$ alkylene; Y is a direct bond or $C_{1-2}$ alkyl; $R^1$ is (i) 5–15 membered cyclic or fused heterocompound comprising 3–14 carbon atmos and one or two atoms selected from a group consisting of nitrogen, oxygen and sulfur, with the proviso that no oxygen-oxygen bond or sulphur-oxygen bond is formed, and which is substituted with one or two substituents selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy; $R^2$ is 5–15 membered cyclic or fused heterocompound comprising 3–14 carbon atoms and one or two nitrogen atoms and, optionally, one oxygen or sulfur atom, and which is substituted with one or two substituents selected from a group consisting of hydrogen, hydroxy, halogen, nitro, hydroxy $C_{1-5}$ alkyl, $C_{1-6}$ alkyl, $C_{3-6}$ alkenyl and halogen $C_{1-4}$ alkoxy; $R^5$ is selected from a group consisting of hydroxy, $C_{1-6}$ alkyl, $C_{3-7}$ cycloalkyl, $C_{3-6}$ alkenyl, halogen $C_{1-6}$ alkyl, halogen $C_{2-6}$ alkenyl and $C_{1-4}$ alkoxy or $R_5$ represents

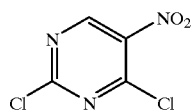

in which $R^6$ is selected from a group consisting of hydrogen, hydroxy, $C_{1-6}$ alkyl, $C_{3-6}$ alkenyl, halogen $C_{1-6}$ alkyl, halogen, nitro and $C_{1-4}$ alkoxy, which comprises:

(a) reacting a compound of the following structure III:

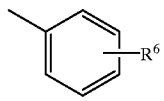
(III)

with a compound of the formula III-a:

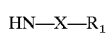
(III-a)

in which X and $R^1$ represent the same as defined above, to give a compound of the formula IV:

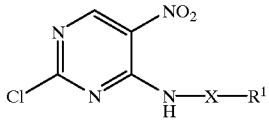
(IV)

in which X and $R^1$ represent the same as defined above, (b) reacting the compound IV with a compound of the formula IV-a:

$Y—R^2$ (IV-a)

in which Y and $R^2$ represent the same as defined above, to give a compound of the formula V:

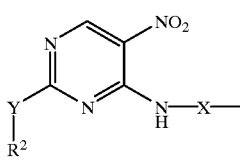
(V)

in which X, $R^1$ and $R^2$ represent the same as defined above, (c) reducing the compound V to give a compound of the formula VI:

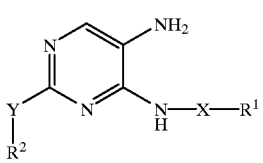
(VI)

in which X, Y, $R^1$, and $R^2$ represent the same as defined above, (d) reacting the compound VI with a compound of the formula (VI-2):

(VI-2)

in which $R^5$ represents the same as defined above, to give the above compound I-B.

4. The process of claim 2, wherein (c) reducing the compound V comprises reacting the compound V with iron and an acid in a polar solvent under reflux.

5. The process of claim 2, wherein (c) reducing the compound V comprises reacting the compound V with iron (Fe) and acetic acid ($CH_3COOH$) in water under reflux.

6. The process of claim 3, wherein (c) reducing the compound V comprises reacting the compound V with iron and an acid in a polar solvent under reflux.

7. The process of claim 3, wherein (c) reducing the compound V comprises reacting the compound V with iron (Fe) and acetic acid ($CH_3COOH$) in water under reflux.

8. A 4,5-diaminopyrimidine derivative selected from the group consisting of
4-benzylamino-5-(2-bromophenylsulfonamido)-2-(IH-tetrazol-I-yl)pyrimidine;

4-benzylamino-5-(2,4-dinitrophenylcarboxamido)-2-(IH-tetrazol-1-yl)pyrimidine;

4-benzylamino-5-(2-hexylcarboxamido)-2-(1H-tetrazol-1-yl)pyrimidine;

and a physiologically acceptable salt thereof.

9. The compound of claim 1 which is selected from a group consisting of

1-[4-benzylamino-5-(2-bromophenylsulfonamido)pyrimidin-2-yl]-4-piperidinecarboxylic acid, 1-[4-benzylamino-5-(4-bromophenylsulfonamido)pyrimidin-2-yl]-4-piperidinecarboxylic acid;

1-[4-benzylamino-5-(4-metylphenylsulfonamido)pyrimidin-2-yl]-4-piperidinecarboxylic acid;

1-[4-benzylamino-5-(2-chlorophenylsulfonamido)pyrimidin-2-yl]-4-piperidinecarboxylic acid;

1-(4-benzylamino-5-hexylcarboxamidopyrimidin-2-yl)-4-piperidinecarboxylic acid;

1-(4-benzylamino-5-ethylsulfonamidopyrimidin-2-yl)-4-piperidinecarboxylic acid;

1-[4-benzylamino-5-trifluoromethylsulfonamidopyrimidin-2-yl)-4-piperidinecarboxylic acid;

ethyl 1-[5-(2-bromophenylsulfonamido)-4-(1,3-dioxaindan-5-yl)methylaminopyrimidin-2-yl]-4-piperidinecarboxylate;

1-[5-(4-chlorophenylsulfonamido)-4-(I,3-dioxaindan-5-yl)methylaminopyrimidin-2-yl]-4-piperidinecarboxylic acid;

5-(4-chlorophenylsulfonamido)-4-(1,3-dioxaindan-5-yl)methylamino-2-(1H-imidazol-1-yl)pyrimidine;

5-ethylsulfonamido-4-(1,3-dioxaindan-5-yl)methylamino-2-(1H-imidazol-1-yl)pyrimidine;

5-hexylcarboxamido-4-(1,3-dioxaindan-5-yl)methylamino-2-(1H-imidazol-1-yl)pyrimidine;

ethyl 1-[5-(4-bromophenylsulfonainido)-4-(1,3-dioxaindan-5-yl)methylaminopyrimidin-2-yl]-4-piperazinecarboxylate-;

5-(4-chlorophenylsulfonamido)-4N-(4-bromobenzylamino)-2-(1H-imidazol-1-yl)pyrimidine;

5-(2-chlorophenylcarboxamido)-4-(1,3-dioxaindan-5-yl)methylamino-2-(1H-2-ethyl-4-methylimidazol-I-yl)pyrimidine;

5-(2,4-dinitrophenylcarboxamido)-4-(1,3-dioxaindan-5-yl)methylamino-2-(H-2-ethyl-4-methylimidazol-1-yl)pyrimidine;

4-benzylamino-5-(2-bromophenylsulfonamido)-2-(4-ethylpiperazino)pyrimidine; and 4-benzylamino-5-(4-chlorophenylsulfonamido)-2-(4-ethylpiperazino)pyrimidine.

\* \* \* \* \*